United States Patent [19]

Hirshowitz et al.

[11] Patent Number: 5,895,656
[45] Date of Patent: Apr. 20, 1999

[54] GAS OR GEL-FILLED SILICONE CUSHION FOR TREATMENT OF KELOID AND HYPERTROPHIC SCARS

[75] Inventors: Bernard Hirshowitz; Ella Lindenbaum; Yaron Har-Shai, all of Haifa, Israel

[73] Assignee: Life Medical Sciences, Inc., Edison, N.J.

[21] Appl. No.: 08/733,235

[22] Filed: Oct. 18, 1996

[51] Int. Cl.$^6$ .......................... A01N 25/34; A61F 13/02; A61L 15/16

[52] U.S. Cl. .............................. 424/402; 424/400

[58] Field of Search ..................... 424/402, 78.02, 424/78.06, 443, 445, 446–449

[56] References Cited

U.S. PATENT DOCUMENTS 5,437,618  8/1995  Sikes ................................ 602/19

Primary Examiner—Thurman K. Page
Assistant Examiner—Kathryne E. Shelborne
Attorney, Agent, or Firm—Henry D. Coleman; R. Neil Sudol

[57] ABSTRACT

The present invention relates to the treatment of keloid and hypertrophic scars by covering the scar with a gas-or gel-filled cushion made of smooth or textured silicone sheeting. It relates particularly to a cushion in the form of a hollow bag filled with completely dry air, inert gel or an inert gas. The invention also relates to a silicone sheeting cushion enclosing silicone beads, polymeric pieces or bodies made of polyfluoroethylene sheeting or a related polymer which produces a negative static charge or, preferably, a silicone sponge or hydrophobic gel, most preferably silicone gel.

16 Claims, 2 Drawing Sheets

GAS OR GEL-FILLED SILICONE CUSHION FOR TREATMENT OF KELOID AND HYPERTROPHIC SCARS

This invention relates to the treatment of keloid and hypertrophic scars by covering the scar with a gas or gel-filled cushion made of silicone sheeting. It relates particularly to a cushion in the form of a hollow bag filled with completely dry air or an inert gas or gel. The invention also relates to a silicone sheeting cushion enclosing silicone beads, polymeric pieces or bodies made of TEFLON sheeting or a related polymer which produces a negative static electrical charge or, preferably, a silicone sponge or gel.

BACKGROUND OF THE INVENTION

Keloid and hypertrophic scars appear on the skin after injury or acne or spontaneously in the shape of a hard bump or swelling which usually causes much distress, both aesthetic and functional, besides pain, it causes both itching and burning sensations and can become a lifelong problem unless medically treated.

Silicone gel or occlusive sheeting is widely used at present for the treatment of hypertrophic and keloid scars without any scientific explanation as to its mode of action. See, Ahn, et al., *Surgery*, 106:781–787 (1989), Mercer N. S. G., *Br J Plast Surg*, 42:83–87, (1989); Perkins, et al., *Burns*, 9:201–204, (1982); Quinn K. J., *Burns*, 13 [Suppl]S33–S40, (1987); Quinn, et al., *Burns*, 12:102–108, (1985); Sawada and Sone, *Br J Plast Surg*, 43:683–688, (1990); and Ohmori, S., *Aesth. Plast Surg* 12:95–99, (1988). With this treatment, softening and flattening of the scar was experienced after from 7 to 12 months of continuous covering of the scar. Professor B. Hirshowitz and other researchers recently noted that rubbing contact with silicone sheeting creates a static electric field which, they believe, acts on the scar, prompting its reversal to normal tissue. See, Hirshowitz, et al., *Eur J Plast Surg.*, 16:5–9, 1993).

The skin and the dermis of hypertrophic and keloid scars are histologically and chemically different from that of intact skin. In the epidermis of these scars the keratin layer is thin or even absent, while in intact skin keratin forms an insulating layer. Paucity of this layer reduces its electrical resistance, and it appears that an electrical charge causes polarization of the ions within the scar and thereby the internal components of the interstitium. The negative ions on the silicone repel circulating negatively charged components in the scar tissue and attract positively charged components. It is also thought that the electrical field may reduce the concentration of mast cells which appear in those scars during proliferation. In short, it is postulated that treatment of this type of scar by tightly covering it with a layer of a soft sheet of silicone causes softening of the keloid matter by reducing the number of mast cells, by reducing the blood flow and by softening the scar. It is the main object of the present invention to provide a non-invasive treatment for hypertrophic and keloid scars which would shorten the time of scar involution by many months.

It is reasoned that increasing of the static electric field (negative charge) applied to the scar could hasten the inhibitory healing process and shorten the time until involution of the scar occurs.

SUMMARY OF THE INVENTION

A silicone cushion has been designed with the purpose of increasing a negative static electric charge in order to accelerate the regression process for hypertrophic and keloid scars. The invention comprises the manufacture of a flexible hollow cushion made of a soft smooth or textured silicone sheeting of a thickness between about 0.1 and 5 mm, preferably about 0.5 and 2 mm, having a hollow space of at least about 2.5 mm, preferably at least about 5 mm and more preferably at least about 10 mm height filled with an inert gas or with completely dry air. An improved effect, i.e. yet a stronger electric field, can be obtained by including in the gas-filled space a number of silicone beads preferably of about 1 mm diameter or small pieces or bodies of "TEFLON™"-sheeting or made of a polymer which produces a significant negative static charge such as polyvinylchloride, polypropylene, polyethylene, polyurethane, celluloid polymers, polyester and acetate rayon, among others.

An improved effect can also be obtained by inserting into the hollow space a similar hollow body of smaller dimensions, similarly filled with an inert gas, dry air or a hydrophobic gel, preferably a silicone gel or oils. The gel, being hydrophobic, substantially prevents condensation of water vapour in the pillow which is the cause of the rapid decay of the negative electrical charge on the pillow surface. Preferably, a stronger electric field is created by the inclusion of a silicone sponge in the hollow space of the cushion or alternatively, by filling the hollow space of the cushion with a hydrophobic gel, preferably silicone gel.

A preferred method of producing the cushion is by connecting two sheets of silicone of identical size along their common edges into a gas-tight body and inflating it with gas by means of a hypodermic needle or even more preferably, filling it with a hydrophobic gel, preferably a silicone gel. After withdrawal of the needle the hole created by insertion of the needle is sealed with glue.

Another method for producing the cushion includes closing the two ends of a flexible silicone tube by gluing them together. The resulting tube cushion is filled with gas or gel as above.

When materials for the production of stronger electric fields, such as silicone beads, TEFLON sheeting, silicone sponges, or related bodies of an appropriate polymeric material or a hydrphobic gel, are to be enclosed in the cushion, they are inserted before the edges of the sheets or ends of the tube are sealed.

By placing the cushion onto the keloid scar and bandaging it in the correct position, involution of the scar is generally experienced within within a few weeks or months.

DETAILED DESCRIPTION OF THE INVENTION

Figure 1:
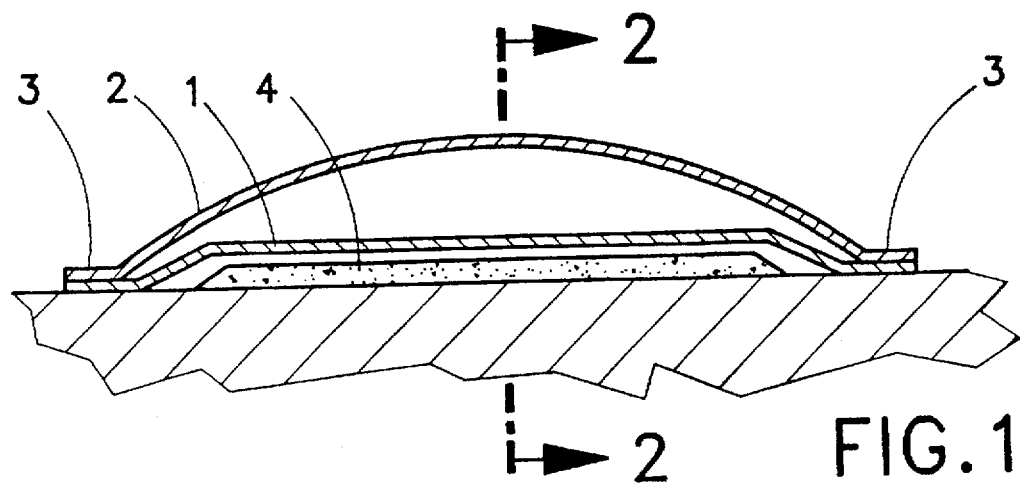
FIG. 1 is a longitudinal section of a cushion of the kind described covering a scar on an extremity.

The following terms are used throughout the specification to describe the present invention.

The term "silicone" is used to describe film, sheeting, beads or pieces of polymer in any form which is made from inert, non-reactive silicone, for example, polydimethylsiloxane or related polysiloxane materials (represented generally by the structure $R_2$—Si—O—, where R is a monovalent organic radical, including for example, a methyl, ethyl, propyl or phenyl group, among others and which may be several or thousands of —Si—O— units or more in length). Physical properties of the silicones depend on the size and type of the monovalent radical used as well as the molecular configuration of the polymer (linear, cyclic, degree of crosslinking, etc.). These silicones are effective for generating a negative static electric field when used in cushions according to the present invention. In the case of silicone gel, this term is used to describe polysiloxane or related silicone polymeric material in the form of gel, wherein the weight average molecular weight chains of the polysiloxane are of a length which is consistent to form a gel-like material (about 200 to 30,000 cps), including, for example, silicone oil. In the other forms, the type of polysiloxane used is generally elastomeric and consistent with the intended use, as sheeting, as beads, or related material. It is noted that polyfluoroethylene may also be used in the present invention as a substitute for polysiloxane material in all the forms used in the present invention.

The term "TEFLON" is used to describe polyfluoroethylene polymers which are used in the present invention.

The term "beads" or "grains" is used to describe polymeric material which is inserted into a hollow space of an inflated cushion according to the present invention for their ability to further increase the strength of the static electrical field generated by the present invention. Numerous polymeric materials may be used in the beads of grains according to the present invention and include, for example, silicone elastomeric material or gel and polyfluoroethylene polymers as generally described hereinabove, as well as polyvinylchoride, polyethylene, polypropylene, polyurethane, celluloid polymers and polyester, among others.

The term "gel" is used to describe hydrophobic material in gel form which may be used to fill the hollow space of an inflated cushion according to the present invention. Hydrophobic gels are preferably hydrophobic polymeric materials having a limited chain-length or weight average molecular weight and are used because of their tendency to reduce or substantially eliminate water vapor condensation which may occur within the hollow area of the cushion. These gels generally have viscosities within the range of about 200 centipoise units to about 30,000 centipoise units. Although any hydrophobic gel or gel-like material may be used in the present invention, gels which are derived from polyfluoroethylene or silicone polymers, e.g., polydisiloxane or related inert silicone polymers are preferred, with those gels derived from silicone being especially preferred.

The term "dry gas" is used to describe gas which is found inside the internal space of the cushion and which contains a substantial absence of water or humidity such that the gas will not have an appreciable or substantial impact on the static electrical field generated by the cushion according to the present invention. While any inert gas may be used in the present invention, in preferred embodiments, the gas is dry air.

The term "smooth" and "textured" is used to describe the polymeric materials which are used in the present invention. Smooth sheeting or other forms of polymeric material which comprise the cushions of the present invention may contain an absence of deformity on the surface of the material (smooth). Textured sheeting or other forms of polymeric material may preferably comprise an irregular surface (textured) containing for example, corners, indentations or related textural features which may be regular or irregular in shape and appearance. In the case of smooth, regular surfaces, such as plane or spherical surfaces, static electrical charges distribute themselves uniformly. In the case of irregular surfaces (textured), there results a non-uniform distribution of charge, and charges will tend to accumulate at the irregular sites. Such non-uniform distributions give rise to non-uniform electric potential. Since the electric field depends on the gradient of the potential, large values of electric field are generated at these non-uniform sites and are advantageous in certain embodiments according to the present invention. See, *Methods in Mathematical Physics*, Lindenbaum, s., (World Scientific Publications, Singapore, 1996), pp 237–240.

Figure 2:
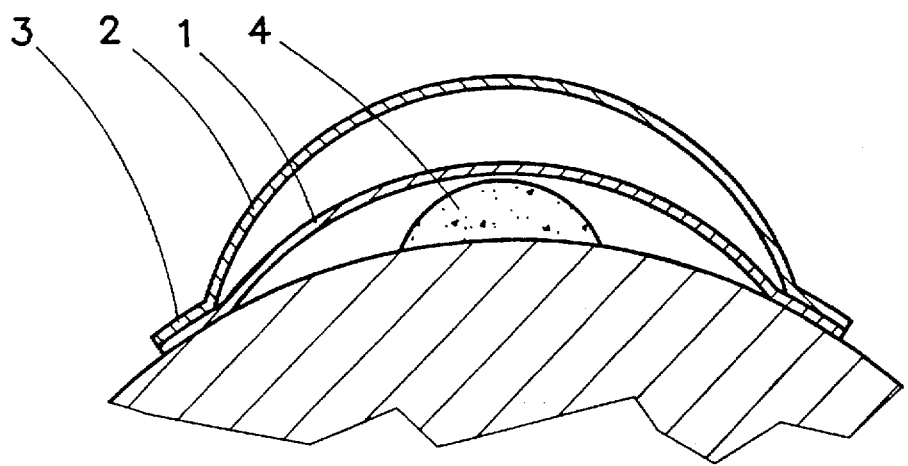
FIG. 2 is a section along line 2—2 of FIG. 1.

Referring to FIGS. 1 and 2 of the drawings an embodiment of a silicone cushion comprises an inner layer 1 and an outer layer 2 of flexible smooth or textured silicone sheeting which has a preferred thickness of between 0.5 and 2 mm, but may be made to other dimensions as needed. The sheet material used is preferably a composition of pure silicone, i.e., polydimethylsiloxane or a related silicone elastomer. Other polymeric materials which generate a significant negative static charge on the surface of the cushion, for example, TEFLON polymers, may also be used in the present invention. For practical reasons, and because of the elastomeric quality of the polydimethylsiloxanes, these are preferred polymers for use in the present invention.

The size of the cushion is chosen in accordance with the length of the scar 4 (in FIGS. 1 and 2) to be covered; the shape may be rectangular, oval or oblong with rounded end portions. The scar is preferably at least substantially covered by the cushion, and more preferably, at least some part of the cushion overlaps areas outside the boundaries of the scar to be treated. The two layers are tightly connected along their common edges 3 in FIGS. 1 and 2. Any method of forming a gas-tight seal may be used including stitching, gluing and heat-sealing, with heat-sealing the preferred method. Examples of glues suitable for this purpose are household adhesive 100X silicone, available under-the Trade Name "DAP" and silicone adhesive sealant, available under the Trade Name of "PERMATEX CLEAR R.T.V." Numerous other glues may also be used. The cushion may be inflated, for example, by inserting a gas under pressure by means of a hypodermic needle. The height of the inflated hollow space should not be less than about 5 mm, more preferably not less than about 10 mm, and can be increased according to the conditions of the scar and bandaging requirements. The preferred gas is completely dry air which can be refilled since air from the original filling is apt to slowly escape through the slightly porous sheet material. Other suitable gases include nitrogen or any inert gas which are inert to the silicone material.

Figure 3:
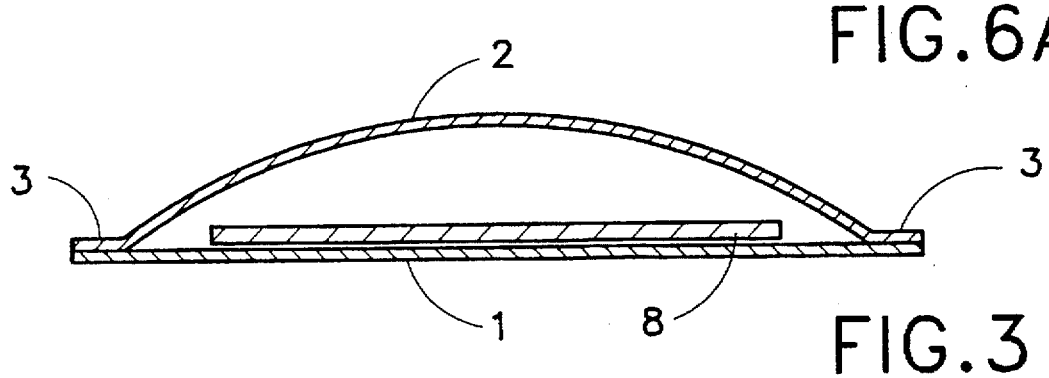
FIG. 3 is a longitudinal section of a cushion containing a silicone sponge of the kind described.
Figure 6B:
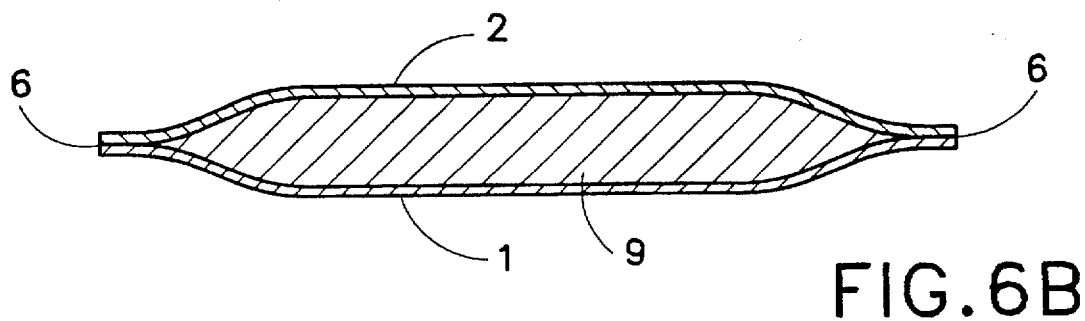
FIG. 6b is a cross section of a cushion filled with gel.

Referring to FIG. 3, the most preferred embodiment of the silicone cushion comprises a silicone sponge 8 of about 6 to about 11 mm thickness, loosely enclosed between the inner 1 and outer 2 layers of smooth or textured silicone sheeting, the sheeting having a most preferred thickness of about 0.6 mm. The silicone sponge is easily compressed and its qualities impart to the cushion a soft and pliable consistency. The edges of the cushion 3 are sealed, for example, with clear RTV adhesive sealant (Permatex 66B). In these custom-made pillows, the sealed edges can be covered with a hypoallergenic material, such as hypoallergenic selfadhesive fabric for comfort (e.g. Fixomull Stretch, Beiersdorf AG., Germany). Friction or deformation by a stretching, rubbing or pumping action with a finger on the pillow, or active body movements like breathing, in proximity to the scar overlaid with the pillow, elicits negatively charged static electricity.

It is known that although silicone itself is a non-conductive material, rubbing or motion of a silicone sheet along cloth or even human skin creates a negatively charged electric field. A field of much increased strength is created with the instant gas- or gel-filled cushion in which the outer layer of the cushion which is separated from the inner layer by dry air, gel or by an inert gas. Readings of the electric field created by the described embodiments were taken with a static fieldmeter which is made by Charleswater W. Newton Company, Boston, Mass., U.S.A. Measurement of the static electric field found that there was a considerable increase in the strength of the field over that of a silicone sheet, up to 3 kV per square inch with cushion alone and up to 7 kV per square inch with a cushion enclosing a silicone sponge or hydrophobic gel. This increase is believed to be the main cause for the rapid involution which, up to now, was not attained by any other means. Experiments have shown that this effect decreases strongly as soon as there exists humidity inside the cushion, even if the gas itself is inert. In addition, under constant environmental conditions, one can obtain different ranges of charge depending upon the location of the pillow. For example, there will be a marked difference in the range of the charge on a table top, on the body and when the cushion is suspended in the air. The differences in charges which are obtained based upon location are related to the speed of decay of the static electrical field. In the case of the cushion on the table top and on the body, the decay of the electrical field is faster, whereas in the the case of the cushion suspended in air, the rate of decay is significantly slower.

Figure 4:
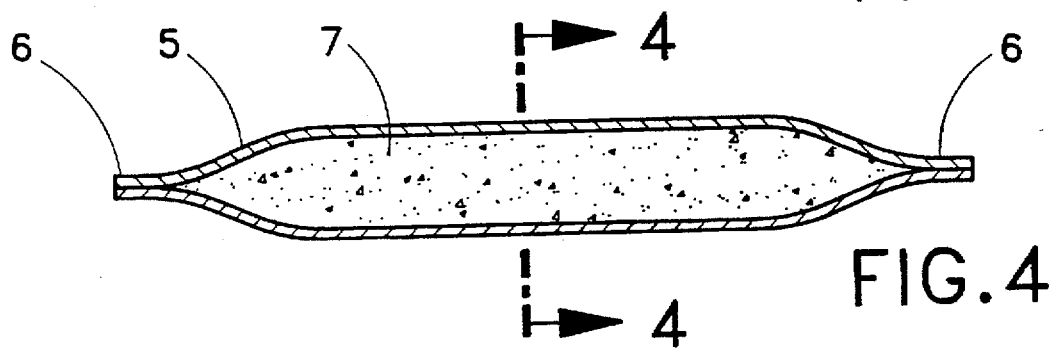
FIG. 4 is a longitudinal section of a cushion made from a flexible tube.
Figure 5:
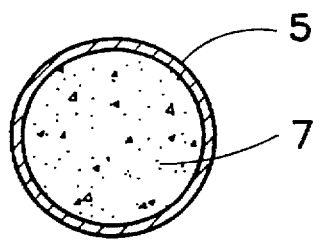
FIG. 5 is a section along line 4—4 of FIG. 3.
Figure 6A:
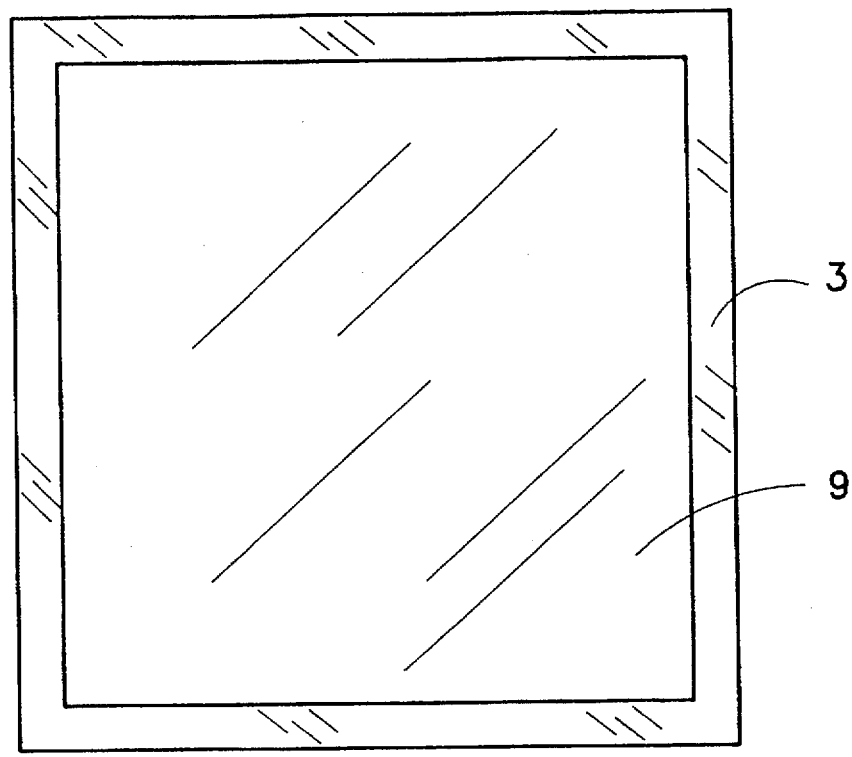
FIG. 6a is an overall view of a textured gel-filled cushion according to the present invention.

Another embodiment of the cushion is illustrated in FIGS. 4 and 5, wherein a short piece of tubing (5) made of suitable silicone is closed at both ends 6 and tightly occluded by heat, a suitable glue or alternative means. In an alternative embodiment, the end may be stoppered by plugs of the same material which are to be glued into the ends, again by silicone glue. The tube material should be thin, smooth or textured and flexible to permit covering of a scar and for securing it tightly.

FIGS. 4 and 5 show a few grains or pieces 7 of dry material inserted into the hollow space, preferably beads of silicone or small pieces of firm TEFLON™-sheeting. The inclusion of these beads further increases the strength of the electrical field by friction with the surrounding sheeting.

Yet another embodiment includes either a piece of silicone sheeting, an inflated bag of silicone or silicone foam inserted into the hollow space of the cushion. In an alternative and preferred embodiment, a silicone sponge or gel may be inserted into the hollow space. Enclosing a layer of silicone sponge or gel within the external envelope of the silicone pillow amplifies the regeneration of the static electric field on the silicone envelope.

Still another embodiment of the invention is a quilted cushion formed by connecting the inner and the outer layer of silicone sheeting in two, three or more points. This can be achieved by sealing the silicone sheets at a given point, for example, by placing glue at those points before connecting the sheets along their edges.

The shape and size of all cushions has to be selected in accordance with the size and length of the keloid scar and its position on the body or its extremities.

Good contact of the silicone pillow on the scar surface is important and to ensure this, the following two procedures may be used to produce superior results:

1. Overlapping the scar edges by about 1–2 cm of the silicone pillow.
2. Use of tight fitting vests on the trunk, knitted sleeves and elastic netting for the limbs and the design of custom-made compression bindings for scars on the trunk or head.

The compression binding may be made of, for example, Mainat fabric (J. Mainat, Barcelona, Spain), a synthetic woven, elastic material that also is used for the treatment of burn scars. Electrostatic readings obtained from the undersurface of the anchoring fabric give low, negative or neutral readings but rarely a positive reading. A strip of Velcro can be sewn onto the undersurface of the pressure garment, opposite the site of application of the silicone pillow over the scar. A corresponding strip of Velcro, when glued onto the outer surface of the pillow at this point, allows the pillow to become fixed over the scar by the compression binding.

Often a certain amount of creativity is used to create a suitable compression binding.

Over natural hollows of the body, such as the sternoxiphoid area, the compression binding can be padded with the insertion of any plastic sponge to compensate for the depression and to assure good contact by pressure on the pillow. In such areas, the thicker 11 mm silicone sponge for the cushion is preferred.

Thirty patients with hypertrophic or keloid scarring of diverse etiology were included in a study of the effectiveness of a preferred embodiment of the present invention. The trial extended over a 12 month period, during which three patients were lost to follow-up. All scars which had been present for 4–6 months or more were included.

Three parameters of hardness, elevation and color were examined. Also assessed in the study were subjective complaints such as pain, itching and discomfort.

The average size of the silicone cushions in this trial ranged from 40 to 250 square cm and they were custom made to fit the variety of scar sizes. Personal hygiene was impressed on the patients, who were required to swab the cushion with 95% alcohol and thoroughly dry both the scar area and the pillow. Patients were encouraged to use the pillows for most of the day and night, and if possible the pillows were to be removed only for cleansing. Not all of the patients were able to tolerate the cushion for more than a few hours stretch. No adhesive or micropore tapes were used for fixing the silicone pillows as they invariably led to skin sensitivity.

Table I represents scar location and age of scar of the 27 remaining patients of the trial, the results of treatment, and the length of time to involution. What was evident in 7 patients was the rapid onset of relief of symptoms associated with pallor and flattening and softening of the scars, often commencing within 2–3 weeks after start of treatment. In six cases, the provision of a well-fitted compression binding over the silicone pillow gave a real impetus to the involution process before there had been refractoriness.

Eleven patients received a combination of intralesional cortico-steroid treatment together with the application of the silicone pillows. This combination therapy was unexpectedly successful, seeming to definitely accelerate the involution in 7 of the scars. Four of these patients had, prior to the use of the cushion, received intralesional cortico-steroid injections with no appreciable improvement.

Overall, a 74% involution rate was seen with the silicone pillows usually within a relatively short time of six weeks to 6 months following commencement of therapy. This was particularly encouraging since the pillow was used in some patients only part of the day. Patients whose scars were in exposed parts of the body, such as the face, neck and chest tended to wear the pillows only at home, and some only at night.

In one patient who was particularly sensitive to the wearing of synthetic fabrics, a silicone pillow was placed on a fresh vertical hypertrophic scar of the midline of the lower abdomen, following a hysterectomy. The patient complained of a burning sensation and severe itchiness after wearing the pillow for two days and she was forced to discontinue its use. This was the only such case encountered in our series of 27 patients, the explanation being that the patient, who exhibits some degree of skin sensitivity to all synthetic fabrics, could not tolerate the silicone material. This patient was not included in Table I. In six patients, the response was minimal, patient compliance being perhaps somewhat lacking because of difficulties associated with the wearing of the compression binding and the underlying pillow in hot, humid conditions.

We claim:

1. A method for treating a keloid or hypertrophic scar in human skin comprising:
   (i) affixing to said scar a hollow body of flexible silicone sheeting or film containing an interior space, said interior space being filled with dry gas or a hydrophobic gel; and
   (ii) creating a field of static electricity in proximity to said scar by frictional contact with said body of flexible silicone.

2. The method of claim 1 further comprising administering intralesional corticosteroid treatment to said human.

3. The method of claim 1, wherein said interior space includes a plurality of silicone grains which are freely moveable.

4. The method according to claim 1, wherein said interior space includes a plurality of pieces of polyfluoroethylene sheeting which are freely moveable.

5. The method according to claim 1, wherein said interior space includes a body of flexible silicone which is freely moveable.

6. The method according to claim 5, wherein said flexible silicone is a silicone sponge.

7. The method according to claim 1 wherein said hydrophobic gel is silicone gel.

8. The method according to claim 1, wherein said hollow body comprises a top sheet of silicone and a bottom sheet of silicone, said top sheet and said bottom sheet being sealed together at their edges.

9. The method according to claim 1, wherein said hollow body comprises tubing which has been sealed at each end.

10. A cushion for use in the treatment of keloid and hypertrophic scars in humans comprising a hollow body of flexible silicone sheeting or film having an interior space filled with dry gas and a plurality of silicone grains or polyfluoroethylene grains freely moveable within said interior space.

11. The cushion according to claim 10, wherein said body comprises a top sheet of silicone and a bottom sheet of silicone, said top sheet and said bottom sheet being sealed together at their edges.

12. The cushion according to claim 10 wherein said body comprises tubing which has been sealed at each end.

13. A cushion for use in the treatment of keloid and hypertrophic scars in humans comprising a hollow body of flexible silicone having an interior space filled with dry gas and a second body of flexible silicone within said interior space, said second body being freely moveable within said interior space.

14. The cushion according to claim 13 wherein said second body of flexible material is a silicone sponge.

15. A method for treating a keloid or hypertrophic scar in human skin comprising:
   (i) affixing to said scar a hollow body of flexible silicone sheeting or film containing an interior space, said interior space being filled with silicone gel, and
   (ii) creating a field of static electricity in proximity to said scar by frictional contact with said body of flexible silicone.

16. The method according to claim 15 wherein said silicone gel has a viscosity ranging from about 200 centipoise units to about 30,000 centipoise units.

* * * * *